US012666241B2

(12) United States Patent
Hellmann et al.

(10) Patent No.: US 12,666,241 B2
(45) Date of Patent: Jun. 23, 2026

(54) METHOD FOR OPERATING A TELE-EMERGENCY PHYSICIAN SYSTEM AND TELE-EMERGENCY PHYSICIAN SYSTEM

(71) Applicant: peiker Holding GmbH, Bad Homburg (DE)

(72) Inventors: Benjamin Hellmann, Berlin (DE); Sebastian Timme, Berlin (DE)

(73) Assignee: Peiker Holding GmbH, Bad Homburg (DE)

( * ) Notice: Subject to any disclaimer, the term of this patent is extended or adjusted under 35 U.S.C. 154(b) by 315 days.

(21) Appl. No.: 18/553,009

(22) PCT Filed: Mar. 31, 2022

(86) PCT No.: PCT/EP2022/058617
§ 371 (c)(1),
(2) Date: Sep. 28, 2023

(87) PCT Pub. No.: WO2022/207814
PCT Pub. Date: Oct. 6, 2022

(65) Prior Publication Data
US 2024/0163654 A1 May 16, 2024

(30) Foreign Application Priority Data
Mar. 31, 2021 (DE) ..................... 10 2021 108 165.3

(51) Int. Cl.
| | |
|---|---|
| *H04W 4/90* | (2018.01) |
| *G16H 80/00* | (2018.01) |
| *H04W 84/12* | (2009.01) |
| *H04W 88/04* | (2009.01) |

(Continued)

(52) U.S. Cl.
CPC .............. *H04W 4/90* (2018.02); *G16H 80/00* (2018.01); *H04W 84/12* (2013.01); *H04W 88/04* (2013.01)

(58) Field of Classification Search
CPC ........ G16H 80/00; H04W 36/00; H04W 4/90; H04W 84/12; H04W 88/04; H04W 88/08

(Continued)

(56) References Cited

U.S. PATENT DOCUMENTS

| | | | | |
|---|---|---|---|---|
| 11,700,522 | B2* | 7/2023 | Nagasawa | ............... H04W 4/44 |
| | | | | 455/404.1 |
| 2009/0247835 | A1* | 10/2009 | Voipio | ................... A61B 5/308 |
| | | | | 600/509 |

(Continued)

FOREIGN PATENT DOCUMENTS

| | | | | |
|---|---|---|---|---|
| EP | | 2252115 A1 * | 11/2010 | ............ H04W 48/18 |

OTHER PUBLICATIONS

International Preliminary Report on Patentability for International Application No. PCT/EP2022/058617, dated Oct. 12, 2023, 18 pages.

(Continued)

*Primary Examiner* — Maria El-Zoobi
(74) *Attorney, Agent, or Firm* — Christopher J. Volkmann; KELLY, HOLT & CHRISTENSON PLLC

(57) ABSTRACT
A method for operating a tele-emergency physician system that includes integrating a WLAN-capable ECG device into a first WLAN network provided by a portable router, and providing first aid to an accident victim outside a vehicle. Vital data of the accident victim is transmitted by the portable router from the first WLAN network via a mobile wireless network to a server. The method includes moving the accident victim after the first aid to the and into the vehicle and at the same time switching over the portable router, controlled by a trigger, from its router operation to repeater operation. The portable router connects itself as a repeater to a second WLAN network. Vital data is forwarded by the mobile router via a mobile wireless network to the (Continued)

server, so that vital data acquired by the ECG device are provided in a continuous data stream at the terminal.

20 Claims, 1 Drawing Sheet

(58) Field of Classification Search
  USPC ......................................................... 455/404.1
  See application file for complete search history.

(56) References Cited

U.S. PATENT DOCUMENTS

| | | | |
|---|---|---|---|
| 2010/0017471 A1* | 1/2010 | Brown ..................... | H04W 4/02 |
| | | | 709/204 |
| 2012/0123224 A1 | 5/2012 | Packer et al. | |
| 2016/0140299 A1* | 5/2016 | Al Harbi ................. | G16Z 99/00 |
| | | | 705/2 |
| 2016/0344983 A1* | 11/2016 | Yoshimura ............... | H04N 5/77 |
| 2017/0300654 A1 | 10/2017 | Stein et al. | |
| 2021/0173529 A1* | 6/2021 | Mostaert ................. | H04W 4/90 |
| 2021/0258300 A1* | 8/2021 | Eriksson ............... | H04L 9/3228 |
| 2022/0406460 A1* | 12/2022 | Golan .................... | G16H 50/20 |
| 2023/0186633 A1* | 6/2023 | Sim ........................ | G10L 15/26 |
| | | | 348/143 |

OTHER PUBLICATIONS

International Search Report and Written Opinion for International Application No. PCT/EP2022/058617 dated Jul. 20, 2022, 17 pages.

* cited by examiner

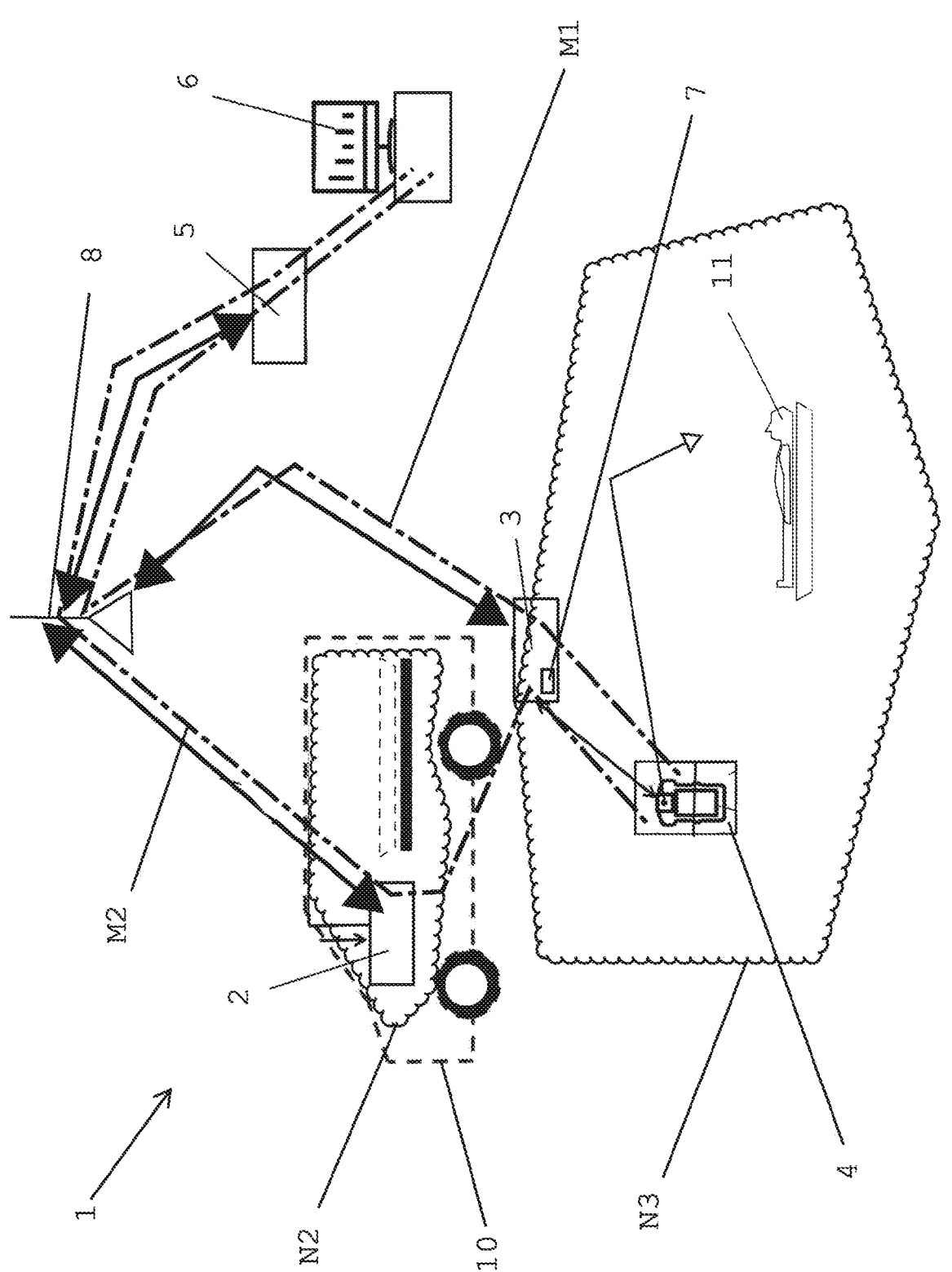

METHOD FOR OPERATING A TELE-EMERGENCY PHYSICIAN SYSTEM AND TELE-EMERGENCY PHYSICIAN SYSTEM

CROSS-REFERENCES TO RELATED APPLICATIONS

This Application is a Section 371 National Stage Application of International Application No. PCT/EP2022/ 058617, filed Mar. 31, 2022, and published as WO 2022/ 207814 A1 on Oct. 6, 2022, and claims priority to German Application No. 102021108165.3, filed Mar. 31, 2021, the contents of these applications are hereby incorporated by reference in their entirety.

BRIEF DESCRIPTION OF THE DRAWINGS

FIG. 1 shows a schematic view of a tele-emergency physician system according to one example.

DETAILED DESCRIPTION

The present disclosure relates to a method for operating a tele-emergency physician system according to the preamble of claim 1 and a tele-emergency physician system as claimed in claim 7.

Systems which describe the transmission of vital data acquired by an ECG device to an emergency physician not located at the usage location are presently in testing. Such a system is described, for example, in the result report "2020-12-18_Telenotarzt-Bayern_Ergebnisbericht [2020-12-18_tele-emergency physician-Bavaria_result-report]" of a project of IQ Medworks GmbH. This report is retrievable under the URL https://innovationsfonds.g-ba.de/downloads/ projekt-dokumente/36/2020-12-18_Telenotarzt-Bayern_Er-gebnisbericht.pdf.

It is an object of the present disclosure to propose a method for operating a tele-emergency physician system, which enables the most interruption-free telemedical care of a patient possible, who is moved into a rescue vehicle after first aid at an accident location. Furthermore, it is an object of the present disclosure to propose a tele-emergency physician system which enables interruption-free telemedical care of a patient who is moved into a rescue vehicle after first aid at an accident location.

This object is achieved by the features of claim 1 or 7, respectively. Advantageous and expedient refinements are specified in the respective dependent claims.

The method according to one example for operating a tele-emergency physician system, which comprises a mobile router arranged in a vehicle, a portable router usable remotely from the vehicle, a server, and a terminal for an emergency physician connected to the server, comprises the steps:

integrating a WLAN-capable ECG device or the like into a first WLAN network provided by the portable router;

providing first aid to an accident victim outside the vehicle, wherein vital data of the accident victim acquired by the ECG device are transmitted from the portable router in router operation from the first WLAN network via a mobile wireless network, in which the portable router is integrated, to the server, in order to provide these data at the terminal;

moving the accident victim after the first aid to the and into the vehicle and at the same time trigger-controlled switching over of the portable router from its router operation to repeater operation, where the portable router connects itself for this purpose as a repeater to a second WLAN network provided by the mobile router, forwarding the vital data acquired by the ECG device from the portable router in the repeater operation from the first WLAN network of the portable router via the second WLAN network of the mobile router to the mobile router and forwarding the vital data from the mobile router via a mobile wireless network via an existing radio link to the server, so that vital data acquired by the ECG device are provided in a continuous data stream at the terminal. By way of such a method, in which the WLAN-capable ECG device is connected by means of the portable router alternately directly via a mobile wireless network or via a second WLAN network indirectly via a mobile wireless network to a server, it is possible to avoid a WLAN connection having to be reestablished for the WLAN-capable ECG device and in this way a significant interruption of the connection to the server having to be accepted. This interruption is avoided by a connection transfer—also called handover—in which the portable router, to which the WLAN-capable ECG device is connected via WLAN, changes from router operation to repeater operation. This is possible significantly faster using the existing protocols and available routers and also can be automated better than logging the WLAN-capable ECG device out of a first WLAN network and subsequently logging the WLAN-capable ECG device into a second WLAN network.

Having the connection of the portable router via the mobile router and the mobile wireless network operationally ready for the server before the portable router ends its router operation is also provided. In this way, it is ensured that the data stream is transferred on at least one path to the server and is thus available at the terminal.

Initiating the switching over by the trigger at earliest when a stable WLAN connection has been established between the portable router and the mobile router is also provided. In this way, it is ensured that an undesirably large gap in the data transmission does not occur due to excessively early switching over.

Furthermore, initiating the switching over by the trigger only when an active transmission of vital data by the portable router via the mobile router and the mobile wireless network to the server also already takes place is provided. In this way, it is ensured that the ECG device already works and supplies vital data upon switching over, so that possibly required troubleshooting is simplified.

Initiating the switching over by the trigger when a corresponding command of the server is also sent to the portable router is also provided, wherein this command is first executed when at least one other switchover procedure, for example, automatically switching over from a camera worn on the body to a vehicle camera has taken place. In this way, it can be indirectly confirmed that the patient is already in the vicinity of the rescue vehicle or has already been moved into the rescue vehicle, so that, for example, excessively early switching over, in the case of which the portable router cannot yet reliably be permanently logged into the second WLAN network, is prevented.

Finally, initiating switching over of the trigger when a communication connection between the vehicle and the portable router is also established is provided, wherein the communication connection is established by short-range communication modules, for example by Bluetooth low-power modules in particular. It can also be indirectly confirmed in this way that the patient is already in the vicinity of the rescue vehicle or has already been moved into the rescue vehicle, so that, for example, excessively early switching over, in the case of which the portable router cannot yet reliably be permanently logged into the second WLAN network, is prevented.

The tele-emergency physician system according to one example comprises a mobile router, a portable router, an ECG device or the like, a server, a terminal, and a trigger, wherein the ECG device is wirelessly connected to the portable router, wherein the server and the terminal are connected to one another, wherein the portable router operates in a first operating mode in router operation such that a connection to the server is established via a mobile wireless network, so that vital data acquired by the ECG device are retrievable as a continuous data stream at the terminal, wherein the portable router operates in a second operating mode in repeater operation such that a connection to the server is established via a WLAN network of the mobile router and the mobile wireless network, so that the vital data acquired by the ECG device are retrievable as a continuous data stream at the terminal, wherein the trigger is designed such that it switches over the portable router from the first operating mode to the second operating mode, wherein this takes place depending on at least one signal received and/or measured value acquired by the trigger. By way of such a tele-emergency physician system, in which the WLAN-capable ECG device is alternately connected by means of the portable router directly via a mobile wireless network or via a second WLAN network indirectly via a mobile wireless network to a server, it is possible to avoid a WLAN-connection having to be reestablished to the WLAN-capable ECG device and in this way a significant interruption of the connection to the server having to be accepted. This interruption is avoided by a connection transfer—also called handover—in which the portable router, to which the WLAN-capable ECG device is connected via WLAN, changes from router operation to repeater operation. This is possible significantly faster using the existing protocols and available routers and also can be automated better than logging the WLAN-capable ECG device out of a first WLAN network and subsequently logging the WLAN-capable ECG device into a second WLAN network.

Finally, operating the portable router at least during the switching over in the first operating mode and in the second operating mode for uninterrupted transfer of the continuous data stream is provided. In this way, it is ensured that the data stream is transferred on at least one path to the server and is thus available at the terminal.

In the meaning of the present disclosure, an ECG device or the like is understood as a medical device which continuously acquires vital data and/or data connected thereto and outputs these data as a continuous data stream.

In the meaning of the present disclosure, a trigger is understood as a switchover device, which switches over the portable router from router operation to repeater operation on the basis of at least one signal and/or measured value.

A mobile wireless network is possibly also to be understood in the meaning of the present disclosure as a satellite communication system or any other data wireless system for longer ranges.

FIG. 1 shows a rough sketch and schematic of a tele-emergency physician system 1. The tele-emergency physician system 1 comprises a mobile router 2, a portable router 3, a WLAN-capable ECG device 4, a server 5, a terminal 6, and a trigger 7. The ECG device 4 is wirelessly connected via WLAN to the portable router 3, wherein the connection is established in a first WLAN network N3, which is provided by the portable router 3. The server 5 and the terminal 6 have a wireless or wired communication connection. The portable router 3 operates in a first operating mode M1 in router operation such that a connection to the server 5 is established via a mobile wireless network 8, so that vital data acquired by the ECG device 4 are retrievable as a continuous data stream at the terminal 6. In a second operating mode M2, the portable router 3 operates such that via a second WLAN network N2, which is provided by the mobile router 2, and via the mobile wireless network 8, to which the mobile router 2 is connected, a connection to the server 5 is established, so that vital data acquired by the ECG device 4 are retrievable as a continuous data stream at the terminal 5. The portable router 3 is switched over in an event-dependent manner from the first operating mode M1 to the second operating mode M2 by the trigger 7. This takes place depending on at least one signal received and/or measured value acquired by the trigger. For uninterrupted transfer of the continuous data stream which the ECG device 4 generates, the portable router 3 operates at least during the switching over in the first operating mode M1 and in the second operating mode M2.

Of course, the portable router 2 and the mobile router 3 can also be connected to the server using different mobile wireless networks.

The method according to one example for operating the tele-emergency physician system 1 comprises the steps:

integrating the WLAN-capable ECG device 4 into the first WLAN network N3 provided by the portable router 3;

providing first aid to an accident victim 9 outside a vehicle 10, wherein vital data of the accident victim 9 acquired by the ECG device 4 are transmitted from the portable router 3 in router operation from the first WLAN network N3 via a mobile wireless network 8, in which the portable router 3 is integrated, to the server 5, in order to provide these data at the terminal 6;

moving the accident victim 9 after the first aid to the and into the vehicle 10 and at the same time switching over, prompted by a trigger 7, the portable router 3 from its router operation to repeater operation, wherein the portable router 3 connects itself for this purpose as a repeater 11 to the second WLAN network N2 provided by the mobile router 2, forwarding the vital data acquired by the ECG device 4 from the portable router 3 in the repeater operation from the first WLAN network N3 of the portable router 3 via the second WLAN network N2 of the mobile router 2 to the mobile router 2 and forwarding the vital data from the mobile router 2 via a mobile wireless network 8 via an existing radio link to the server 5, so that vital data acquired by the ECG device are provided in a continuous data stream at the terminal.

An intermediate step is optionally provided, in which the connection of the ECG device 2 via the portable router 3, the mobile router 2, and the mobile wireless network 8 to the server 5 is ready for operation before the portable router 3 ends its router operation.

Although the present invention has been described with reference to preferred embodiments, workers skilled in the art will recognize that changes may be made in form and detail without departing from the spirit and scope of the invention.

LIST OF REFERENCE SIGNS 1 tele-emergency physician system
2 mobile router 3 portable router
4 WLAN-capable ECG device
5 server
6 terminal
7 trigger
8 mobile wireless network
9 accident victim
10 vehicle
11 repeater
M1 first operating mode (router operation)
M2 second operating mode (repeater operation)
N3 first WLAN network constructed from 3
N2 second WLAN network constructed from 2
The invention claimed is:

1. A method for operating a tele-emergency physician system, the tele-emergency physician system comprises:

a mobile router arranged in a vehicle, a portable router used remotely from the vehicle in a router operating mode, a server, and a terminal, connected to the server, the method comprises:

integrating a WLAN-capable ECG device into a first WLAN network provided by the portable router;

providing first aid to an accident victim outside the vehicle, wherein vital data of the accident victim acquired by the ECG device is transmitted by the portable router in the router operating mode from the first WLAN network via a mobile wireless network, into which the portable router is integrated, to the server, to provide these data at the terminal;

moving the accident victim after the first aid to the vehicle and into the vehicle and, at the same time, switching over the portable router, controlled by a trigger, from the router operating mode to a repeater operating mode, wherein the portable router in the repeater operating mode connects itself as a repeater to a second WLAN network provided by the mobile router; and forwarding the vital data acquired by the ECG device by the portable router in the repeater operating mode from the first WLAN network of the portable router via the second WLAN network of the mobile router to the mobile router and forwarding the vital data by the mobile router via the mobile wireless network via an existing radio link to the server, so that vital data acquired by the ECG device is provided in a continuous data stream at the terminal.

2. The method as claimed in claim 1, wherein forwarding the vital data by the mobile router via the mobile wireless network via the existing radio link to the server includes connecting the portable router, via the mobile router and the mobile wireless network, to the server, and wherein the portable router is connected to the server before the portable router ends the router operating mode.

3. The method as claimed in claim 1, wherein the trigger initiates the switching over at earliest when a stable WLAN connection is established between the portable router and the mobile router.

4. The method as claimed in claim 1, wherein the trigger initiates the switching over when active transmission of vital data by the portable router via the mobile router and the mobile wireless network to the server already takes place.

5. The method as claimed in claim 1, wherein the trigger initiates the switching over when a corresponding command of the server is also sent to the portable router, and wherein the corresponding command is executed when at least one other switchover procedure has taken place.

6. The method as claimed in claim 1, wherein the trigger initiates the switching over when a communication connection is also established between the vehicle and the portable router, wherein the communication connection is established by short-range communication modules.

7. A tele-emergency physician system comprising:

a mobile router positioned within a vehicle, a portable router used remotely from the vehicle in a first operating mode, an ECG device that acquires vital data and is wirelessly connected to the portable router, a server in operative communication with the mobile router, a terminal in operative communication with the server, and a trigger in operative communication with the portable router, wherein the portable router operates in the first operating mode, the first operating mode includes a router operation such that a first connection to the server is established via a first WLAN network provided by the portable router and a mobile wireless network, so that the vital data acquired by the ECG device is retrievable as a continuous data stream at the terminal via the first connection, wherein the portable router operates in a second operating mode, the second operating mode including a repeater operation such that a second connection to the server is established via a second WLAN network of the mobile router and the mobile wireless network, so that the vital data acquired by the ECG device is retrievable as a continuous data stream at the terminal via the second connection, and wherein the trigger switches over the portable router from the first operating mode into the second operating mode, and wherein the switching over takes place depending on at least one signal received and/or measured value acquired by the trigger.

8. The tele-emergency physician system as claimed in claim 7, wherein the portable router operates in the first operating mode and the second operating mode during the switching over for uninterrupted transfer of the continuous data stream.

9. The method as claimed in claim 5, wherein the at least one other switchover procedure comprises automatically switching over a body camera to a vehicle camera.

10. The method as claimed in claim 6, wherein the short-range communication modules comprise Bluetooth low-power modules.

11. The tele-emergency system as claimed in claim 7, wherein the ECG device connects to either the first WLAN network or the second WLAN network based on the at least one signal received and/or measured value acquired by the trigger.

12. A tele-emergency physician system comprising:

a first router used remotely from a vehicle, the first router operates in a first operating mode to provide a first WLAN network;

a second router used within the vehicle, the second router provides a second WLAN network;

an ECG device that acquires patient vital data, wherein the ECG device is integrated into the first WLAN network created by the first router;

a trigger that switches the first router from the first operating mode to a second operating mode, wherein, when the first router operates in the second operating mode, the first router connects to the second WLAN network provided by the second router, and wherein the first router transmits the patient vital data from the first WLAN network to the second WLAN network;

a server that receives the patient vital data from one of: the first WLAN network provided by the first router, or the second WLAN network provided by the second router; and a terminal in operative communication with the server, wherein the terminal receives the patient vital data from the server.

13. The tele-emergency physician system of claim 12, wherein the first operating mode is a router operating mode and wherein the second operating mode is a repeater operating mode.

14. The tele-emergency physician system of claim 12, wherein the trigger switches the first router from the first operating mode to the second operating mode based on at least one event-dependent signal obtained by the trigger.

15. The tele-emergency physician system of claim 12, wherein the trigger switches the first router from the first operating mode to the second operating mode when the first router is moved to a location inside of the vehicle.

16. The tele-emergency physician system of claim 15, wherein the first router, in the second operating mode, connects itself as a repeater to the second WLAN network.

17. The tele-emergency physician system of claim 12, wherein the trigger initiates switching the first router from the first operating mode to the second operating mode when a communication connection is established between the vehicle and the first router.

18. The tele-emergency physician system of claim 12, wherein the patient vital data is transmitted from the server to the terminal via a mobile wireless network.

19. The tele-emergency physician system of claim 18, wherein the mobile wireless network includes an existing radio link between the server and the terminal.

20. The tele-emergency physician system of claim 19, wherein the terminal is located remote from the vehicle.

* * * * *